United States Patent [19]
Larson et al.

[11] Patent Number: 5,641,562
[45] Date of Patent: Jun. 24, 1997

[54] WATER-SHRINKABLE FILM

[75] Inventors: Jennifer Cappel Larson, Fond du Lac; Dave Allen Soerens, Neenah, both of Wis.

[73] Assignee: Kimberly-Clark Worldwide Inc., Neenah, Wis.

[21] Appl. No.: 367,652

[22] Filed: Dec. 30, 1994

[51] Int. Cl.$^6$ .................................................. B32B 27/00
[52] U.S. Cl. .................. 442/394; 428/284; 524/35; 524/37; 524/47; 525/57; 525/187; 525/203; 525/204; 525/221; 604/358
[58] Field of Search ........................... 428/284, 286; 525/333.2, 57, 203, 204, 221, 187; 604/358; 524/35, 37, 47

[56] References Cited

U.S. PATENT DOCUMENTS

| | | | |
|---|---|---|---|
| 3,952,347 | 4/1976 | Comerford et al. | 6/335 |
| 4,166,464 | 9/1979 | Korpman | 128/287 |
| 5,116,667 | 5/1992 | Zimmerman et al. | 428/220 |

FOREIGN PATENT DOCUMENTS

| | | |
|---|---|---|
| 0525245A1 | 2/1993 | European Pat. Off. . |
| 0604730A1 | 7/1994 | European Pat. Off. . |
| 1483838 | 8/1977 | United Kingdom . |

OTHER PUBLICATIONS

Computer printout of Literature Search Results — Topic, "Water/Moisture Shrinkables" by Jennifer Cappel, Feb. 24, 1994.

*Primary Examiner*—James J. Bell
*Attorney, Agent, or Firm*—John R. Schenian

[57] ABSTRACT

Disclosed is a water-shrinkable film prepared from a composition comprising an elastomeric polymer and a water-dispersible polymer. Also disclosed is a disposable absorbent product, intended for the absorption of body fluids, including the film. The film is useful in imparting improved water-shrinkability properties to the disposable absorbent product.

18 Claims, 1 Drawing Sheet

WATER-SHRINKABLE FILM

BACKGROUND OF THE INVENTION

1. Field of the Invention

The present invention relates to a flexible polymeric film which shrinks rapidly in size when immersed in water. The film may be used in a disposable absorbent product to impart improved flushability properties to the product after the product's use.

2. Description of the Related Art

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a topsheet, a backsheet, and an absorbent structure between the topsheet and backsheet. These products usually include some type of fastening system for fitting the product onto the wearer.

Disposable absorbent products are typically subjected to one or more liquid insults, such as of water, urine, menses, or blood, during use. As such, the outer cover materials of the disposable absorbent products are typically made of non-liquid-soluble materials, such as polypropylene films, that exhibit a sufficient strength and handling capability so that the disposable absorbent product retains its integrity during use by a wearer.

Although current disposable baby diapers and other disposable absorbent products have been generally accepted by the public, these products still have need of improvement in specific areas. For example, many disposable absorbent products can be difficult to dispose of. For example, attempts to flush many disposable absorbent products down a toilet into a sewage system typically lead to blockage of the toilet or pipes connecting the toilet to the sewage system. In particular, the outer cover materials typically used in the disposable absorbent products generally do not disintegrate or disperse when flushed down a toilet so that the disposable absorbent product cannot be disposed of in this way.

As such, there is a need for new materials that may be used in disposable absorbent products that generally retain their integrity and strength during use; but after such use, the disposable absorbent product may be easily and efficiently disposed of by flushing the disposable absorbent product down a toilet. Such a disposable absorbent product would then be capable of being degraded by a liquid sewage system as compared to having to be disposed of into a landfill or other solid waste disposal system.

SUMMARY OF THE INVENTION

The present invention concerns a film that substantially shrinks in surface area when contacted with an excess amount of water. Such a film may be used in a disposable absorbent product to increase the flushability of the product into a liquid sewage system.

One aspect of the present invention concerns a film comprising an elastomeric polymer and a water-dispersible polymer, wherein the film exhibits desired water-shrinkability properties.

One embodiment of such a film comprises from greater than 0 to less than 100 weight percent of an elastomeric polymer and from greater than 0 to less than 100 weight percent of a water-dispersible polymer, wherein all weight percents are based on the total amount of the elastomeric polymer and the water-dispersible polymer present in the film, and wherein the film exhibits a loss in surface area, when immersed in an excess of water for about 15 minutes, of at least about 15 percent.

In another aspect, the present invention concerns a disposable absorbent product comprising the film disclosed herein.

One embodiment of such a disposable absorbent product comprises a liquid-permeable topsheet, a backsheet attached to the liquid-permeable topsheet, and an absorbent structure positioned between the topsheet and the backsheet, wherein the backsheet comprises the film of the present invention.

DETAILED DESCRIPTION OF THE PREFERRED EMBODIMENTS

Figure 1:
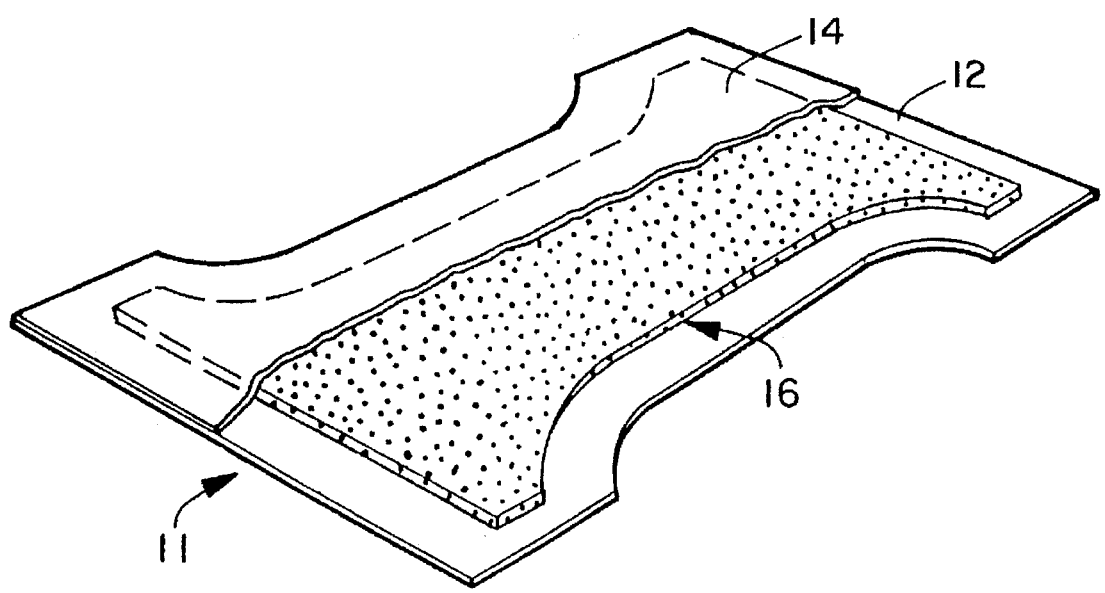
FIG. 1 represents a disposable absorbent product according to the present invention.

The present invention, in one aspect, concerns a film material that exhibits desired water-shrinkable properties and is prepared from an extrudable composition. The film generally comprises an elastomeric polymer and a water-dispersible polymer.

As used herein, the term "water-dispersible polymer" is meant to refer to a polymer which when placed in an aqueous environment will, with sufficient time, disperse into the aqueous environment. As such, a material prepared from such a water-dispersible polymer which when is placed in an aqueous environment will, with sufficient time, break apart into smaller pieces. As a result, the water-dispersible polymer once dispersed within the aqueous environment may be more advantageously processable in recycling processes or flushable in, for example, septic and municipal sewage treatment systems. If desired, the dispersal of the water-dispersible polymer may be hastened by the use of agitation and/or certain triggering means, such as pH, as further discussed below. The actual amount of time needed for dispersal of the water-dispersible polymer will typically depend at least in part upon the particular end-use design criteria. Typically, the water-dispersible polymer will be fully dispersed within the aqueous environment into which the water-dispersible polymer has been placed within about 60 minutes, suitably within about 15 minutes, more suitably within about 5 minutes, and most suitably within about 30 seconds.

Examples of materials useful as the water-dispersible polymer in the present invention include hydroxypropyl cellulose, polyethylene oxide, polyvinyl alcohol, polyvinyl pyrolidone, polyvinyl pyridine, gelatinized starch, nylon copolymer, polyacrylic acid, or mixtures thereof.

The water-dispersible polymer should be used in the film in an amount effective to achieve the desired water-shrinkability properties. The water-dispersible polymer will be present in the film of the present invention in an amount from greater than 0 to less than 100 weight percent, suitably from about 25 to about 97 weight percent, more suitably from about 35 to about 95 weight percent, and most suitably from about 55 to about 95 weight percent of the total weight of the elastomeric polymer and the water-dispersible polymer present in the film.

As used herein, the term "elastomeric polymer" is meant to refer to a polymer which has the ability to be stretched from its original length and to retract very rapidly upon release of the stretching force to approximately its original length and, as used herein, wherein the polymer is not water-dispersible.

In particular, as used herein, the terms "elastic" and "elastomeric" are used interchangeably to mean that property of a polymer which, upon application of a biasing force, permits the polymer and, optionally, a material prepared from the polymer, to be stretchable to a stretched, biased length which is at least about 125 percent, that is about 1.25 times, its relaxed, unbiased length, and which will cause the polymer or material to recover at least 40 percent of its elongation upon release of the stretching, elongating force. A hypothetical example which would satisfy this definition of an elastomeric material would be a one (1) inch sample of a material which is elongatable to at least 1.25 inches and which, upon being elongated to 1.25 inches and released, will recover to a length of not more than 1.15 inches. Many elastomeric polymers or materials prepared from such polymers may be stretched by much more than 25 percent of their relaxed length and many of these will recover to substantially their original relaxed length upon release of the stretching, elongating force. This latter class of polymers or materials is generally beneficial for purposes of the present invention.

The term "recover" relates to a contraction of a stretched polymer or material upon termination of a biasing force following stretching of the polymer or material by application of the biasing force. For example, if a material having a relaxed, unbiased length of about one (1) inch were elongated about 50 percent by stretching to a length of about 1.5 inches, the material would have been elongated about 50 percent and would have a stretched length that is about 150 percent of its relaxed length. If this exemplary stretched material contracted, that is, recovered to a length of about 1.1 inches after release of the biasing and stretching force, the material would have recovered about 80 percent (about 0.4 inch) of its elongation.

Examples of polymers useful as the elastomeric polymer in the present invention include natural rubber; synthetic rubbers such as nitrile rubber, butyl rubber, polysulfide rubber, cis-i,4-polyisoprene, ethylene-propylene terpolymers, silicone rubber, polyurethane rubber, and thermoplastic rubbers such as uncrosslinked polyolefins; synthetic thermosetting polymers such as styrene-butadiene copolymers, polychloroprene (neoprene), nylon copolymers, spandex fibers comprising segmented polyurethane, ethylene-vinyl acetate copolymer; and mixtures thereof.

A number of block copolymers can be used as the elastomeric polymer of this invention. Such block copolymers generally comprise an elastomeric midblock portion and a thermoplastic endblock portion. The block copolymers used in this invention generally have a three-dimensional physical crosslinked structure below the endblock portion glass transition temperature ($T_g$) and are elastomeric. The block copolymers are also thermoplastic in the sense that they can be melted above the endblock $T_g$, formed, and resolidified several times with little or no change in physical properties (assuming a minimum of oxidative degradation).

One way of synthesizing such block copolymers is to polymerize the thermoplastic endblock portions separately from the elastomeric midblock portions. Once the midblock and endblock portions have been separately formed, they can be linked. Typically, midblock portions can be obtained by polymerizing di- and tri-unsaturated $C_4$-$C_{10}$ hydrocarbons such as, for example, dienes such as butadiene, isoprene, and the like, and trienes such as 1,3,5-heptatriene, and the like. When an endblock portion A is joined to a midblock portion B, an A-B block copolymer unit is formed, which unit can be coupled by various techniques or with various coupling agents C to provide a structure such as A-B-A, which is believed to comprise two A-B blocks joined together in a tail-to-tail A-B-C-B-A arrangement. By a similar technique, a radial block copolymer can be formed having the formula $(A-B)_nC$, wherein C is the hub or central, polyfunctional coupling agent and n is a number greater than 2. Using the coupling agent technique, the functionality of C determines the number of A-B branches.

Endblock portion A generally comprises a poly (vinylarene), such as polystyrene, having an average molecular weight between about 1,000 and about 60,000. Midblock portion B generally comprises a substantially amorphous polyolefin such as polyisoprene, ethylene/propylene polymers, ethylene/butylene polymers, polybutadiene, and the like, or mixtures thereof, having an average molecular weight between about 5,000 and about 450,000. The total molecular weight of the block copolymer is suitably about 10,000 to about 500,000 and more suitably about 200,000 to about 300,000. Any residual unsaturation in the midblock portion of the block copolymer can be hydrogenated selectively so that the content of olefinic double bonds in the block copolymers can be reduced to a residual proportion of less than 5 percent and suitably less than about 2 percent. Such hydrogenation tends to reduce sensitivity to oxidative degradation and may have beneficial effects upon elastomeric properties.

Suitable block copolymers used in this invention comprise at least two substantially polystyrene endblock portions and at least one substantially ethylene/butylene midblock portion. Ethylene/butylene typically comprises the major amount of the repeating units in such a block copolymer and can constitute, for example, 70 percent by weight or more of the block copolymer. The block copolymer, if radial, can have three or more arms, and good results can be obtained with, for example, four, five, or six arms. The midblock portion can be hydrogenated, if desired.

Linear block copolymers, such as A-B-A, A-B-A-B-A, or the like, are suitably selected on the basis of endblock content, large endblocks being preferred. For polystyrene-ethylene/butylene-polystyrene block copolymers, a styrene content in excess of about 10 weight percent is suitable, such as between about 12 to about 30 weight percent. With higher styrene content, the polystyrene endblock portions generally have a relatively high molecular weight. A commercially available example of such a linear block copolymer is a styrene-ethylene/butylene-styrene block copolymer which contains about 13 weight percent styrene units and essentially the balance being ethylene/butylene units, commercially available from the Shell Chemical Company, under the trade designation KRATON G1657 elastomeric resin. Typical properties of KRATON G1657 elastomeric resin are reported to include a tensile strength of 3400 pounds per square inch ($23 \times 10^6$ kilograms per square meter), a 300 percent modulus of 350 pounds per square inch ($1.4 \times 10^5$ kilograms per square meter), an elongation of 750 percent at break, a Shore A hardness of 65, and a Brookfield viscosity of a toluene solution of about 4200 centipoise at room temperature.

The elastomeric polymer should be used in the film in an amount effective to achieve the desired water-shrinkability properties. The elastomeric polymer will be present in the film of the present invention in an amount from greater than 0 to less than 100 weight percent, suitably from about 3 to about 75 weight percent, more suitably from about 5 to about 65 weight percent, and most suitably from about 5 to about 45 weight percent of the total weight of the elastomeric polymer and the water-dispersible polymer present in the film.

A film of the present invention generally has the structure of a continuous sheet of material, with no identifiable, individual fibers or the like. The film will suitably comprise a single layer comprising a mixture of both the water-dispersible polymer and the elastomeric polymer. Alternatively, the film may comprise at least two layers with a first layer comprising the water-dispersible polymer and a second layer comprising the elastomeric polymer.

Films are known to be prepared by a variety of processes such as, for example, extrusion processes and casting processes. In general, the film of the present invention may be prepared from a thermoplastic composition that comprises the water-dispersible polymer and the elastomeric polymer. As used herein, the term "thermoplastic" is meant to describe a material that softens when exposed to heat and which substantially returns to its original condition when cooled to room temperature.

While the principal components of the film of the present invention have been described in the foregoing, such film is not limited to such principal components, and can include other components not adversely effecting the desired water-shrinkability properties of the film. Exemplary materials which could be used as additional components include, without limitation, pigments, antioxidants, plasticizers, stabilizers, surfactants, waxes, flow promoters, solid solvents, particulates, and materials added to enhance processability of the film.

It is desirable that the film of the present invention exhibit desirable water-shrinkable properties. In particular, the film of the present invention will exhibit a desired loss in surface area when immersed in an excess of water. As used herein, the term "immersed" is intended to represent that a material is substantially completely submerged into or otherwise substantially completely surrounded by the water. As used herein, the term "excess of water" is intended to represent that the amount of water into which a material is immersed is effective to substantially completely surround the material being immersed and wherein any amount of water absorbed by the material being immersed represents an insubstantial amount of the total amount of water being used. As such, the amount of water used to immerse the material must be sufficiently large so as to take into consideration the amount of water that may be absorbed by the material during its immersion and subsequent shrinking.

A film of the present invention will exhibit a loss in surface area that is at least about 15 percent, suitably at least about 20 percent, more suitably at least about 30 percent, and most suitably at least about 50 percent, as calculated in relation to the original surface area of the film prior to immersion in water, when immersed in an excess of water for a period of time. Thus, as an example, a film that has an initial surface area of about 1 square inch will exhibit a final surface area after having been immersed in water for a period of time that will be less than about 0.85 square inch, suitably less than about 0.8 square inch, more suitably less than about 0.1 square inch, and most suitably less than about 0.5 square inch. The loss in surface area exhibited by a film material may be quantified as the Water-Shrinkability value of the film material, defined in the Test Methods section herein.

A film of the present invention will typically exhibit its desired loss in surface area when immersed in an excess of water for a time period of less than about 15 minutes, suitably for a time period of less than about 5 minutes, more suitably for a time period of less than about 1 minute, and most suitably for a time period of less than about 30 seconds.

A film of the present invention will generally exhibit its desired loss in surface area when immersed in an excess of water wherein the water is at any temperature effective to result in the desired loss in surface area of the film. Typically, the water will be at a temperature of between about 0° C. to about 100° C., suitably between greater than 0° C. to about 50° C., and more suitably between about 5° C. to about 40° C.

It is generally believed that the water-shrinkability of a film of the present invention occurs in the following manner. The film comprises a mixture of the water-dispersible polymer and the elastomeric polymer wherein the elastomeric polymer is under tension and temporarily maintained in such a tensioned state by the dry water-dispersible polymer. As the film is immersed in an excess of water, the water-dispersible polymer absorbs some of the water and generally becomes solvated, thus becoming relatively mobile within the film such that the water-dispersible polymer releases the elastomeric polymer from its tensioned state. The contraction of the elastomeric polymer generally results in the film exhibiting a decrease in surface area.

A number of factors have been found or are believed to affect the water-shrinkable properties of a film of the present invention. Such factors may include, for example, the conditions under which the film is prepared. Such process conditions could include the actual process used such as a cast process or a blown process, the linespeed, the extruder speed, or the blow up ratio (for blown films). Stretching of the film after preparation may also affect the water-shrinkable properties of the film. Stretch conditions that may affect the water-shrinkable properties of the film include the amount, rate, wind tension, and rest period afterwards, of stretching. Such process or stretch conditions are generally believed to affect the amount of tension placed on the elastomeric polymer present in the film, which is believed to ultimately affect the amount of water-shrinkability the film will exhibit when immersed in an excess of water.

The physical characteristics of the prepared film may also have an affect on the water-shrinkable properties of the film. Such physical characteristics include the chemical and physical properties of the components of the film, the difference in chemical and physical properties between the components of the film, the relative amounts of each component of the film, the morphology or homogeneity of the film, and the gauge or thickness of the film.

Another factor found to affect the water-shrinkability of a film is the pH of the water solution into which the film is immersed. In one embodiment of the present invention, the film will generally exhibit its water-shrinkability property under a wide range of pH values. Typically, the water into which the film is to be immersed will be at a pH that is suitably between about 1 to about 14, more suitably between about 3 to about 12, and most suitably between about 5 to about 9.

In another embodiment of the present invention, the film will generally exhibit its water-shrinkability property only above or below a specific pH value. By selectively choosing the materials to be used as the water-dispersible polymer and the elastomeric polymer, a film prepared from such materials may be found to exhibit the desired water-shrinkability properties under specific pH conditions. For example, it may be possible to prepare a film that substantially maintains its original surface area while being used in a water solution that has a pH below some critical value; but when the pH of the water solution is changed to, or the film is disposed of into a different water solution having a pH above the critical value, the film will undergo the desired change in surface area. For example, the film will only exhibit its desired water-shrinkability property when the water into which the film is to be immersed has a pH that is suitably above about 8.5, more suitably above about 9, and most suitably above about 9.5.

The film of the present invention may generally be of any size or dimension as long as the film exhibits the desired water-shrinkability properties as described herein. Generally, the film will have a thickness of less than about 0.1 inch (0.25 centimeter), suitably less than about 0.05 inch (0.13 centimeter), and more suitably less than about 0.01 inch (0.03 centimeter).

The film of the present invention may also be used or combined with other film materials, with the film of the present invention being used as a separate layer or as an individual zone or area within a larger, composite film material. The film of the present invention may be combined, for example, with a typical liquid-impermeable barrier film material, such a polypropylene film. When such a combination is placed into an aqueous environment, the water-shrinkability property of the film of the present invention may result in a loss in surface area of the entire film combination or in a delamination of the film of the present invention from the typical liquid-impermeable barrier film material.

The film materials of the present invention may be combined with other film materials by methods well known to those skilled in the art, such as by using adhesives or simply by layering the different film materials together and holding together the composite materials with, for example, stitching or by application of heat and pressure.

In one embodiment of the present invention, a disposable absorbent product is provided, which disposable absorbent product comprises a liquid-permeable topsheet, a backsheet attached to the topsheet, and an absorbent structure positioned between the topsheet and the backsheet, wherein the backsheet comprises the film of the present invention.

While one embodiment of the invention will be described in terms of the use of a film material in an infant diaper, it is to be understood that the film material is equally suited for use in other disposable absorbent products known to those skilled in the art.

FIG. 1 illustrates a disposable diaper 11 according to one embodiment of the present invention. Disposable diaper 11 includes a backsheet 12, a topsheet 14, an absorbent structure 16 positioned between the backsheet 12 and the topsheet 14, wherein the backsheet 12 comprises a film of the present invention.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of additional materials suitable, in addition to the film of the present invention, for use as the backsheet are liquid-impervious materials, such as polyolefin films, as well as vapor-pervious materials, such as microporous polyolefin films.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time. It is desired that when a disposable absorbent product includes the film of the present invention, the film substantially maintains its original surface area during use of the disposable absorbent product. As such, the amount of liquid insulting the disposable absorbent product during use should not be of such an excessive amount that the film will undergo a substantial change in surface area during use of the disposable absorbent product.

After the disposable absorbent product has been used, it will be desirable to dispose of the disposable absorbent product. If the disposable absorbent product includes the film of the present invention, it may be possible to dispose of the product directly to a liquid disposal system, such as by disposing of the product into a toilet. When placed into a toilet, an excess of water will generally be present such that the film of the present invention may undergo a rapid surface area change. The disposable absorbent product may then be capable of being flushed down the toilet without fear of the disposable absorbent product clogging the piping of the toilet. By this method of disposal, the disposable absorbent product may then be successfully treated and degraded by the sewage system to which the toilet is attached instead of disposing of the disposable absorbent product through a solid waste disposable system. By not having to be disposed of through a solid waste disposable system, the use of the film of the present invention may reduce the amount of solid waste that has to be landfilled, incinerated, or otherwise disposed of.

TEST PROCEDURES

Water-Shrinkability

A rectangular, four liter borosilicate glass basin, available from the Corning Glass Works under the trade designation Pyrex, is used. The basin is filled with about 3 liters of room temperature (about 22° C.) distilled water. A rectangular silicone platform, having a thickness of about 0.75 inch (about 1.9 centimeters), a width of about 6 inches (about 15 centimeters), and a length of about 6 inches (about 15 centimeters) is placed inside, at the bottom of, the basin. A rectangular, low density polyethylene mesh screen having thickness of about 0.04 inch (about 0.1 centimeter), a length of about 13 inches (about 33 centimeters), a width of about 8 inches (about 20 centimeters), and a mesh size that is about 0.2 centimeter by about 0.2 centimeter square, is attached to the silicone platform with two pins such that the mesh screen may float along the length of the pins to the surface of the water.

Material samples are cut to a desired size and placed onto the floating mesh screen. A third pin is used to attach the mesh screen to the silicone platform such that the mesh screen and the material sample remain immersed in the water. At desired time increments, the third pin is removed so that the mesh screen and the material sample float to the surface of the water. While immobile on the mesh screen on the surface of the water, the length and width dimensions of the material sample may be measured. The mesh screen and the material sample are then again immersed and the mesh screen attached to the silicone platform with the third pin so that additional measurements of the material sample may be made. The process is then repeated for desired time periods. With the measured length and width dimensions of the material sample at various points in time, the change in surface area over time may be calculated.

The Water-Shrinkability value for an evaluated material sample, for a specific period of time, is given as the difference in surface areas exhibited by the material sample initially and then subsequently after evaluation, divided by the original surface area, and multiplied by 100 percent, as represented by the formula:

Water Shrinkability value =

$$\frac{\text{Surface Area(Original)} - \text{Surface Area(After Time)}}{\text{Surface Area(Original)}} \times 100\%$$

EXAMPLES

Example 1

Sample films were prepared from compositions including an elastomeric polymer and a water-dispersible material.

For Sample 1 films, the elastomeric copolymer was an ethylene-vinyl acetate copolymer, comprising about 70 percent of vinyl acetate, having a density at about 23° C. of about 1.08 gram per cubic centimeter, and having a melt index of about 5 grams per 10 minutes (as measured according to ASTM D 1238, Method E), commercially available from the Miles Company under the trade designation Levapren 700HV ethylene-vinyl acetate copolymer. The water-dispersible material was polyethylene oxide, having a molecular weight of about 200,000 and a viscosity range as a 5 weight percent aqueous solution at about 25° C. of about 65 to about 115 centipoise, commercially available from the Union Carbide Company under the trade designation Polyox WSR N-80 water-soluble resin.

For Sample 2 films, the elastomeric copolymer was a linear styrene-isoprene-styrene block copolymer, which contains about 22 weight percent styrene units and essentially the balance being isoprene units, having a midblock $T_g$ of about $-50°$ C., a tensile strength of about 2900 pounds per square inch, and specific gravity of about 0.93, commercially available in pellet form from the Shell Chemical Company, under the trade designation KRATON D1111 elastomeric copolymer. The water-dispersible material was polyethylene oxide, having a molecular weight of about 200,000 and a viscosity range as a 5 weight percent aqueous solution at about 25° C. of about 65 to about 115 centipoise, commercially available from the Union Carbide Company under the trade designation Polyox WSR N-80 water-soluble resin.

As a control material, a sample was prepared using polyethylene oxide, having a molecular weight of about 200,000 and a viscosity range as a 5 weight percent aqueous solution at about 25° C. of about 65 to about 115 centipoise, commercially available from the Union Carbide Company under the trade designation Polyox WSR N-80 water-soluble resin.

The elastomeric copolymer and the water-dispersible material were first melt blended together with a plasticizer. The plasticizer was polyoxyethylene sorbitan monolaurate, having a specific gravity of about 1.1 and a boiling point above 100° C., available from ICI Americas Inc. under the trade designation Tween 20 polyoxyethylene sorbitan monolaurate. The blend was then extruded to form a film having a thickness of about 0.003 inch (about 0.008 centimeter). The blends were extruded using a die temperature of about 240° F., a melt temperature of about 290° F., an extruder speed of about 28 to about 33 revolutions per minute for a 2.5 inch diameter screw, and a linespeed of between about 50 to about 200 feet per minute. Film samples having a width of about 1.75 inches (about 4.4 centimeters) and a length of about 2.0 inches (about 5.1 centimeters), for a surface area of about 3.5 square inches (about 22.6 centimeters), were cut out.

The film samples were then measured for changes in surface area over time, as represented by Water-Shrinkability values, by using the Water-Shrinkability test method described herein. The results of this evaluation are shown in Table 1. The control sample essentially completely dispersed within about 1 second after being immersed into the water and, as such, it was impossible to measure any change in surface area.

The amount of surface area shrinkage of a film sample was found to depend, at least, on the amount and type of elastomeric copolymer used to prepare the film. As can be seen from Table 1, for Sample 1 films greater shrinkage occurs with smaller amounts of the ethylene-vinyl acetate elastomeric copolymer. For Sample 2 films, more shrinkage generally occurs at relatively low or high amounts of the styrene-isoprene-styrene elastomeric block copolymer. Furthermore, the Sample 2 films having a relatively low amount (about 5 to about 20 weight percent) of the styrene-isoprene-styrene elastomeric block copolymer were observed to disperse somewhat as well as shrink when immersed in the water.

The aspect ratio (ratio of width to length) of the shrunk films was also measured and the results are shown in Table 2. All of the films initially would have had an aspect ratio of about 0.875. A final aspect ratio different than 0.875 indicates that a sample film did not shrink symmetrically. As can be seen from Table 2, the final aspect ratio, and thus the character of the shrinkage that the film exhibits, is dependent, at least, on the amount and type of elastomeric copolymer used to prepare the film.

A Sample 1 film, wherein the ethylene-vinyl acetate copolymer was used in an amount of about 30 weight percent of the total composition and the polyethylene oxide was used in an amount of about 70 weight percent of the total composition, was immersed in water and its surface area measured as a function of time. The film sample had a thickness of about 0.003 inch (about 0.008 centimeter), a width of about 1.75 inches (about 4.4 centimeters) and a length of about 2.0 inches (about 5.1 centimeters), for a surface area of about 3.5 square inches (about 22.6 centimeters). The results of this evaluation are shown in Table 3.

A majority of the shrinkage is seen to occur within about 500 seconds, with additional shrinkage occurring over a longer period of time. It was observed that no significant weight loss from the film occurs after about 1 hour of immersion. However, after several days of immersion, the film exhibits a weight loss of about 30 percent.

TABLE 1

Water-Shrinkability Value of Films After 15 Minute Water Immersion

| Sample | Percent Elastomeric Polymer in Sample Composition | | | | | | | | |
|---|---|---|---|---|---|---|---|---|---|
| | 5 | 10 | 15 | 20 | 25 | 30 | 35 | 40 | 45 |
| Sample 1 | 83 | 80 | 60 | 57 | 51 | 49 | — | — | — |
| Sample 2 | 17 | 26 | 43 | 46 | 37 | 40 | 40 | 37 | 34 |

TABLE 2

Aspect Ratio of Film Samples After
15 Minute Water Immersion

Percent Elastomeric Polymer in Sample Composition

| Sample | 5 | 10 | 15 | 20 | 25 | 30 | 35 | 40 | 45 |
|---|---|---|---|---|---|---|---|---|---|
| Sample 1 | 2.4 | 1.8 | 1.7 | 1.3 | 1.2 | 1.1 | — | — | — |
| Sample 2 | 1.1 | 0.9 | 0.6 | 0.7 | 0.6 | 0.6 | 0.6 | 0.6 | 0.6 |

TABLE 3

Water-Shrinkability Value of a Film as a Function of Time

| | Time (seconds) | | | | | | | |
|---|---|---|---|---|---|---|---|---|
| | 0 | 30 | 60 | 180 | 300 | 900 | 1800 | 3600 |
| Water-Shrinkability Value (Percent) | 0 | 40 | 44 | 46 | 53 | 54 | 60 | 63 |

Example 2

Sample films were prepared from compositions including an elastomeric polymer and a water-dispersible material.

The elastomeric copolymer was a linear styrene-isoprene-styrene block copolymer, which contains about 22 weight percent styrene units and essentially the balance being isoprene units, having a midblock $T_g$ of about −50° C., a tensile strength of about 2900 pounds per square inch, and specific gravity of about 0.93, commercially available in pellet form from the Shell Chemical Company, under the trade designation KRATON D1111 elastomeric copolymer. The water-dispersible material was polyethylene oxide, having a molecular weight of about 200,000 and a viscosity range as a 5 weight percent aqueous solution at about 25° C. of about 65 to about 115, commercially available from the Union Carbide Company under the trade designation Polyox WSR N-80 water-soluble resin.

The elastomeric copolymer and the water-dispersible material were first blended together and extruded to form various films having respective thicknesses of about 0.002 inch (about 0.005 centimeter), about 0.003 inch (about 0.008 centimeter), about 0.004 inch (about 0.010 centimeter), and about 0.005 inch (about 0.013 centimeter). The blends were extruded using a die temperature of about 240° F., a melt temperature of about 290° F., an extruder speed of about 28 to about 33 revolutions per minute for a 2.5 inch diameter screw, and a linespeed of between about 50 to about 200 feet per minute.

Various samples of the respective films were then subjected to a post-extrusion stretching. Samples of the various films were obtained that had a width of about 3 inches (about 7.6 centimeters) and a length of about 6 inches (about 15.2 centimeters). The post-extrusion stretching was done on a machine similar to that used for tensile testing, such as a MTS Sintech 1/D. The load cell used is about 25 pounds (about 11.5 kilograms). The procedure is performed in a room with standard-condition atmosphere such as a temperature of about 23° C. and a relative humidity of between about 30 to about 50 percent.

The film sample is then placed in the pneumatic action grips (jaws) with 1 inch by 3 inch rubber coated grip faces. The gauge length is about 3 inches and the initial crosshead speed is about 500 millimeters per minute. The crosshead speed is the rate at which the upper jaw moves upward stretching the film sample until a desired amount of stretching is achieved. The stretching is reported as the extended length of the film sample, given as a percentage of the original, pre-stretched gauge length.

Film samples having a width of about 1.75 inches (about 4.4 centimeters) and a length of about 2.0 inches (about 5.1 centimeters), for a surface area of about 3.5 square inches (about 22.6 centimeters), were then cut out from the respective stretched films.

The film samples were then measured for changes in surface area, as represented by Water-Shrinkability values, for a time period of about 15 minutes, by using the Water-Shrinkability test method described herein. The results of this evaluation are shown in Table 4.

TABLE 4

Water-Shrinkability Value of Films After
15 Minute Water Immersion

| | Film Thickness (Inches) | | | |
|---|---|---|---|---|
| Post-Extrusion Stretching | 0.002 | 0.003 | 0.004 | 0.005 |
| 0% | 47 | 42 | 36 | 32 |
| 50% | 58 | 52 | 47 | 42 |
| 100% | 52 | 58 | 63 | 47 |
| 150% | 60 | 60 | 60 | 60 |
| 200% | 60 | 60 | 60 | 60 |

The amount of shrinkage of a film sample was found to depend, at least, on the thickness of the film as well as the amount of stretching used to prepare the film. As can be seen from Table 4, greater shrinkage generally occurs with smaller thickness and for a more highly stretched sample. This is believed to occur because of increased orientation of the elastomeric polymer.

Example 3

A sample film was prepared that would exhibit shrinkage only under specific conditions such as at above a specific pH.

The elastomeric copolymer was an ethylene-vinyl acetate copolymer, comprising about 70 percent of vinyl acetate, having a density at about 23° C. of about 1.08 gram per cubic centimeter, and having a melt index of about 5 grams per 10 minutes, commercially available under the Miles Company under the trade designation Levapren 700HV ethylene-vinyl acetate copolymer. The water-dispersible material was an acrylic acid polymer having a molecular weight of about 175,000, a glass transition temperature of about 73° C., a Sward Hardness of about 40, and specific gravity of about 1.18, available from the B.F. Goodrich Chemical Company as solid flakes under the trade designation Carboset 526 acrylic acid copolymer. The ethylene-vinyl acetate copolymer was used in an amount of about 30 weight percent of the total composition and the acrylic acid polymer was used in an amount 25 of about 70 weight percent of the total composition.

The elastomeric copolymer and the water-dispersible material were first melt blended together and extruded to form a film having a thickness of about 0.003 inch (about 0.008 centimeter). The blend was extruded using a die temperature of about 240° F., a melt temperature of about 290° F., an extruder speed of about 28 to about 33 revolutions per minute for a 2.5 inch diameter screw, and a linespeed of between about 50 to about 200 feet per minute.

A film sample having a width of about 1.75 inches (about 4.4 centimeters) and a length of about 2.0 inches (about 5.1 centimeters), for a surface area of about 3.5 square inches (about 22.6 centimeters), was then cut out from the film. The film sample was immersed in water and its surface area measured, as represented by Water-Shrinkability values, as a function of pH of the water. The pH of the water was adjusted by adding amounts of standard soluble buffer powders, available from Micro Essential Laboratory under the trade designation Hydrion pH Buffers in Capsules buffer powder, to obtain a desired pH, up to a pH of about 12. For a pH of about 13, a 0.1N solution of sodium hydroxide was used. Initially, the water was given a pH of about 5 and subsequently increased. The time period of immersion in the water at each pH was about 30 minutes. The results of this evaluation are shown in Table 5.

TABLE 5

Water-Shrinkability Value of a Film as a Function of pH

| | pH | | | | | | | |
|---|---|---|---|---|---|---|---|---|
| | 5 | 6 | 7 | 8 | 9 | 10 | 11 | 12 | 13 |
| Water-Shrinkability Value (Percent) | 0 | 0 | 0 | 0 | 19 | 25 | — | — | 28 |

The amount of shrinkage of the film sample was found to depend on the pH of the water solution into which the film was immersed. As can be seen from Table 5, substantial surface area shrinkage did not occur until a pH of about 9 was reached. This is believed to occur because the water-dispersible polymer used, acrylic acid copolymer, includes carboxylic acid groups and is thus a pH-sensitive polymer, not undergoing any substantial physical changes until the pH reaches a critical level to neutralize the carboxylic acid groups. At this point, the film experiences a sudden change in surface area. Thus, by selective choice of the polymers used to prepare a film of the present invention, the film may be designed to undergo changes in surface area only under desired conditions.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

What is claimed is:

1. A film comprising:
   a. from greater than 0 to less than 100 weight percent of an elastomeric polymer; and
   b. from greater than 0 to less than 100 weight percent of an water-dispersible polymer, wherein all weight percents are based on the total amount of the elastomeric polymer and the water-dispersible polymer present in the film, and wherein the film exhibits a loss in surface area of at least about 15 percent when immersed in an excess of water for less than about 15 minutes.

2. The film of claim 1 wherein the water-dispersible polymer is hydroxypropyl cellulose, polyethylene oxide, polyvinyl alcohol, polyvinyl pyrolidone, polyvinyl pyridine, gelatinized starch, nylon copolymer, polyacrylic acid, or mixtures thereof.

3. The film of claim 2 wherein the water-dispersible polymer is polyethylene oxide.

4. The film of claim 1 wherein the film comprises from about 25 to about 97 weight percent of the water-dispersible polymer.

5. The film of claim 1 wherein the elastomeric polymer is natural rubber, nitrile rubber, butyl rubber, polysulfide rubber, cis-i,4-polyisoprene, a ethylene-propylene terpolymer, silicone rubber, polyurethane rubber, an uncrosslinked polyolefin, a styrene-butadiene copolymer, polychloroprene, a nylon copolymer, a spandex fiber comprising segmented polyurethane, an ethylene-vinyl acetate copolymer, and mixtures thereof.

6. The film of claim 1 wherein the elastomeric polymer is a block copolymer comprising an elastomeric midblock portion and a thermoplastic endblock portion.

7. The film of claim 6 wherein the elastomeric polymer is a styrene-ethylene/butylene-styrene block copolymer.

8. The film of claim 1 wherein the film comprises from about 3 to about 75 weight percent of the elastomeric polymer.

9. The film of claim 1 wherein the film exhibits a loss in surface area of at least about 20 percent.

10. The film of claim 1 wherein the film exhibits a loss in surface area of at least about 50 percent.

11. The film of claim 1 wherein the film is immersed in an excess of water for less than about 5 minutes.

12. The film of claim 1 wherein the film is immersed in an excess of water for less than about 30 seconds.

13. The film of claim 1 wherein the water has a pH between about 1 to about 14.

14. The film of claim 1 wherein the water has a pH between about 5 to about 9.

15. The film of claim 1 wherein the water has a pH above about 8.5.

16. The film of claim 1 wherein the film has thickness less than about 0.1 inch.

17. The film of claim 1 wherein the film is prepared by extrusion.

18. A disposable absorbent product comprising a liquid-permeable topsheet, a backsheet attached to the liquid-permeable topsheet, and an absorbent structure positioned between the liquid-permeable topsheet and the backsheet, wherein the backsheet comprises a film comprising:
   a. from greater than 0 to less than 100 weight percent of an elastomeric polymer; and
   b. from greater than 0 to less than 100 weight percent of an water-dispersible polymer, wherein all weight percents are based on the total amount of the elastomeric polymer and the water-dispersible polymer present in the film, and wherein the film exhibits a loss in surface area of at least about 15 percent when immersed in an excess of water for less than about 15 minutes.

* * * * *